United States Patent [19]

Hazbun

[11] Patent Number: 4,556,749

[45] Date of Patent: * Dec. 3, 1985

[54] CATALYTIC CONVERSION OF OLEFINS TO HIGHER HYDROCARBONS

[75] Inventor: Edward A. Hazbun, Media, Pa.

[73] Assignee: Atlantic Richfield Company, Los Angeles, Calif.

[*] Notice: The portion of the term of this patent subsequent to Feb. 28, 2001 has been disclaimed.

[21] Appl. No.: 601,144

[22] Filed: Apr. 16, 1984

[51] Int. Cl.$^4$ .............................................. C07C 1/00
[52] U.S. Cl. .................................... 585/330; 585/518; 585/519; 585/529; 585/533
[58] Field of Search ............... 585/330, 518, 519, 529, 585/533

[56] References Cited

U.S. PATENT DOCUMENTS

| | | | |
|---|---|---|---|
| 2,484,384 | 10/1949 | Levine et al. | 585/518 |
| 2,694,002 | 11/1954 | Hays | 585/518 |
| 2,843,639 | 7/1958 | Langlois et al. | 585/518 |
| 3,661,801 | 5/1972 | Gutmann et al. | 585/529 |
| 4,153,638 | 5/1979 | Bercik et al. | 585/533 |
| 4,384,157 | 5/1983 | DeGraff | 585/529 |
| 4,393,259 | 7/1983 | Ward et al. | 585/330 |

*Primary Examiner*—Curtis R. Davis
*Attorney, Agent, or Firm*—Craig E. Larson

[57] ABSTRACT

A process for converting normally gaseous olefins to higher hydrocarbons by catalytic oligomerization is disclosed wherein a feedstock comprising said olefins and containing a major amount of alkane diluent is contacted with a heterogeneous acid catalyst to produce said higher hydrocarbons.

1 Claim, No Drawings

CATALYTIC CONVERSION OF OLEFINS TO HIGHER HYDROCARBONS

BACKGROUND OF THE INVENTION

This invention relates to a method of catalytically converting olefins into higher hydrocarbons. This invention more particularly relates to a method for converting feedstocks containing ethylene and $C_3+$ olefins to higher hydrocarbons. This invention also relates to the conversion of methane to higher hydrocarbons.

Recently, it has been discovered that methane may be converted to higher hydrocarbons by a process which comprises contacting methane and an oxidative synthesizing agent at synthesizing conditions (e.g, at a temperature selected within the range from about 500° to about 1000° C.). Oxidative synthesizing agents are compositions having as a principal component at least one oxide of at least one metal which compositions produce $C_2+$ hydrocarbon products, co-product water, and a composition comprising a reduced metal oxide when contacted with methane at synthesizing conditions. Reducible oxides of several metals have been identified which are capable of converting methane to higher hydrocarbons. Oxides of manganese, tin, indium, germanium, lead, antimony and bismuth are particularly useful. See commonly-assigned U.S. patent application Ser. Nos. 522,925 (now U.S. Pat. No. 4,443,649); 522,944 (now U.S. Pat. No. 4,444,984); 522,942 (now U.S. Pat. No. 4,443,648); 522,905 (now U.S. Pat. No. 4,443,645); 522,877 (now U.S. Pat. No. 4,443,647); 522,876 (now U.S. Pat. No. 4,443,644); and 522,906 (now U.S. Pat. No. 4,443,646,) all filed Aug. 12, 1983.

Commonly-assigned U.S. patent application Ser. No. 522,935, filed Aug. 12, 1983, discloses and claims a process which comprises contacting methane with an oxidative synthesizing agent under elevated pressure (e.g., 2-100 atmospheres) to produce greater amounts of $C_3+$ hydrocarbon products.

Commonly-assigned U.S. patent application Ser. No. 522,938, filed Aug. 12, 1983, discloses and claims a process for the conversion of methane to higher hydrocarbons which comprises contacting methane with particles comprising an oxidative synthesizing agent which particles continuously recirculate between two physically separate zones—a methane contact zone and an oxygen contact zone.

Commonly-assigned U.S. patent application Ser. No. 522,937, filed Aug.12, 1983, now U.S. Pat. No. 4,499,322 discloses and claims a process for the conversion of methane to higher hydrocarbons which comprises contacting methane with an oxidative synthesizing agent containing a promoting amount of alkali metal and/or compounds thereof. The entire content of this application is incorporated herein by reference.

Commonly-assigned U.S. patent application Ser. No. 522,936 filed Aug. 12, 1983, now U.S. Pat. No. 4,495,374 discloses and claims a process for the conversion of methane to higher hydrocarbons which comprises contacting methane with an oxidative synthesizing agent containing a promoting amount of alkaline earth metal and/or compounds thereof. The entire content of this application is incorporated herein by reference.

Commonly-assigned U.S. patent application Ser. No. 06/600,665, now U.S. Pat. No. 4,499,323 discloses and claims a process for the conversion of methane to higher hydrocarbons which comprises contacting methane with a contact solid comprising a reducible oxide of praseodymium and at least one member of the group consisting of alkali metals, alkaline earth metals, and compounds thereof. The entire content of this application is incorporated herein by reference.

Commonly-assigned U.S. patent application Ser. No. 06/600,918 discloses and claims a process for the conversion of methane to higher hydrocarbons which comprises contacting methane with a contact solid comprising a reducible oxide of terbium and at least one member of the group consisting of alkali metals, alkaline earth metals, and compounds thereof. The entire content of this application is incorporated herein by reference.

Commonly-assigned U.S. patent application Ser. No. 06/600,917, now U.S. Pat. No. 4,499,324 discloses and claims a process for the conversion of methane to higher hydrocarbons which comprises contacting methane with a contact solid comprising a reducible oxide of cerium and at least one member of the group consisting of alkali metals, alkaline earth metals, and compounds thereof. The entire content of this application is incorporated herein by reference.

Commonly-assigned U.S. patent application Ser. No. 06/600,730 discloses and claims a process for the conversion of methane to higher hydrocarbons which comprises contacting methane with a contact solid comprising a reducible oxide of iron and at least one member of the group consisting of alkali metals, alkaline earth metals, and compounds thereof. The entire content of this application is incorporated herein by reference.

Commonly-assigned U.S. patent application Ser. No. 06/600,669, now U.S. Pat. No. 4,489,215 discloses and claims a process for the conversion of methane to higher hydrocarbons which comprises contacting methane with a contact solid comprising a reducible oxide of ruthenium and at least one member of the group consisting of alkali metals, alkaline earth metals, and compounds thereof.

The reaction products of such processes are mainly ethylene, ethane other light hydrocarbons, carbon oxides, coke and water.

One object of the present invention is a multistage process for converting a gas comprising methane to higher hydrocarbon, preferably normally liquid hydrocarbons.

Another object of the present invention is a method for converting ethylene and $C_3+$ olefins to heavier hydrocarbons. Other objects, aspects and the several advantages of the present invention will be apparent to those skilled in the art upon consideration of the following description of this invention and of the appended claims.

SUMMARY OF THE INVENTION

According to one embodiment of the present invention, normally gaseous olefins are converted to higher hydrocarbons by catalytic oligomerization which comprises contacting a feedstock comprising said olefins and a major amount of alkane diluent with a heterogeneous acid catalyst to produce said higher hydrocarbons. The diluent alkanes (preferably $C_1-C_5$ alkanes) act as a heat sink in the oligomerization zone, thus moderating the adiabatic temperature rise and reducing reactor cost. The oligomerization reactors may be staged, with heat exchangers placed between stages, to further control the temperature and attain quantitative conversion of olefins to higher hydrocarbons, preferably normally liquid hydrocarbons.

The elimination of equipment to separate alkanes from olefins prior to oligomerization is another desirable feature of this invention. The oligomerization reaction is used as a chemical separation means which converts olefins to higher hydrocarbons which are readily separated from lower alkanes in the oligomerization product.

One specific embodiment of the general method of this invention is a process for converting methane to higher hydrocarbon products which comprises:

(a) contacting at a temperature selected within the range of about 500° to 1000° C. a gas comprising methane and at least one reducible oxide of at least one metal which oxides when contacted with methane at said temperature are reduced and produce higher hydrocarbon products and water, said contacting producing an effluent comprising normally gaseous olefins containing a major amount of unreacted methane and other higher normally gaseous alkanes; and (b) oligomerizing said effluent or streams derived from said effluent which contain a major amount of $C_1$-$C_5$ alkanes to produce still higher hydrocarbon products.

DETAILED DESCRIPTION OF THE INVENTION

The feedstock converted to higher hydrocarbons according to this invention contains ethylene and $C_3+$ olefins. In addition, the feedstock contains major amounts (i.e, greater than 50 vol. %) of the lower alkanes, especially $C_1$-$C_5$ alkanes. Examples of non-hydrocarbon components which may also be present include water, carbon oxides (i.e., CO and/or $CO_2$), and the like. The presence of steam in the catalyst reactors zones under the temperature conditions employed may adversely effect the aging and/or the deactivation characteristics of the catalyst employed.

The present invention involves the use of highly dilute olefinic feedstocks. More particularly, it has been found that desirable results may be obtained even though an oligomerization feedstock contains major amounts (i.e., more than 50 vol. %) of lower alkanes. It has further been found that desirable results may be obtained even though the feedstock contains major amounts (i.e., more than 50 vol. %) of methane.

The process of this invention, while not limited thereto in its broader aspects, is suited to oligomerizing feedstocks comprising an olefinic fraction which contains a major amount (i.e., greater than 50 vol. %, preferably greater than 70 vol. %) of ethylene.

Numerous catalysts and processes are known for the oligomerization of olefins generally, and of ethylene particularly. For example, phosphoric acid supported on a kieselguhr base has been widely used for making polymer gasoline (i.e., olefinic hydrocarbon liquids within the gasoline boiling range) from refinery gases. Other catalysts which have been employed for similar purposes include the oxides of cobalt, nickel, chromium, molybdenum and tungsten on supports such as alumina, silica-alumina, kieselguhr, carbon and the like.

Included within the broad scope of the present invention are all catalysts and processes which are effective for the oligomerization of olefins to higher hydrocarbons, preferably olefinic hydrocarbon liquids within the gasoline boiling range. Without intending to limit the scope of the claimed invention, most oligomerization catalysts may be classified in one of two general categories: metal catalysts and acid catalysts. They may also be classified as heterogeneous (solid) catalysts or homogeneous (liquid-phase) catalysts.

For examples of metal catalysts based on nickel, see U.S. Pat. Nos. 2,828,347; 3,459,826; 3,527,839; 3,954,668; 3,959,400; 4,260,844; 4,272,406; 4,288,648; 4,293,725; and *Industrial Chemistry,* 47 pp. 752, et seq. (1955). Note that these catalysts require a donor ligand and a Lewis acid. For examples of metal catalysts based on palladium, see U.S. Pat. Nos. 3,644,565; 3,728,415; 3,738,977; 3,758,626; and 3,920,763. An example of metal catalysts based on chromium is found in U.S. Pat. No. 3,709,954. An example of metal catalysts based on cobalt is found in *Industrial and Engineering Chemistry,* 42, pp. 2580, et seq. (1950). Examples of metal catalysts based on titanium on found in U.S. Pat. Nos. 3,981,941 and 4,110,410. An example of metal catalysts based on tungsten is found in U.S. Pat. No. 3,903,193. An example of metal catalysts based on rhenium is found in U.S. Pat. No. 3,393,251.

Examples of phosphoric acid catalyst are described in U.S. Pat. Nos. 2,383,318 and 3,887,634 and also in *Industrial and Engineering Chemistry,* 27, pp. 1364, et seq. (1935). Acid catalysts based on chlorided or fluorided alumina are found in U.S. Pat. Nos. 3,364,191 and 3,515,769 and also in USSR Patent No. 107,176.

Other acid catalysts of particular interest in the context of the present invention are silaceous, crystalline molecular sieves. Such silica-containing crystalline materials include materials which contain, in addition to silica, significant amounts of alumina. These crystalline materials are frequently named "zeolites", i.e., crystalline aluminosilicates. Silica-containing crystalline materials also include essentially aluminum-free silicates. These crystalline materials are exemplified by crystalline silica polymorphs (e.g., silicalite, disclosed in U.S. Pat. No. 4,061,724 and organosilicates, disclosed in U.S. Pat. No. Re. 29948), chromia silicates (e.g., CZM), ferrosilicates and galliosilicates (see U.S. Pat. No. 4,238,318), and borosilicates (see U.S. Pat. Nos. 4,226,420; 4,269,813; and 4,327,236).

Crystalline aluminosilicate zeolites are best exemplified by ZSM-5 (see U.S. Pat. Nos. 3,702,886 and 3,770,614), ZSM-11 (see U.S. Pat. No. 3,709,979), ZSM-12 (see U.S. Pat. No. 3,832,449), ZSM-21 and ZSM-38 (see U.S. Pat. No. 3,948,758), ZSM-23 (see U.S. Pat. No. 4,076,842), and ZSM-35 (see U.S. Pat. No. 4,016,246). Examples of processes for the conversion of low molecular weight olefins over zeolites are found in U.S. Pat. Nos. 2,972,643; 3,325,465; 3,960,978; 3,972,832; 4,021,502; 4,044,065; 4,150,062; and 4,254,295. Also see U.S. Pat. Nos. 4,417,086 and 4,417,087 wherein oligomerization processes employing fluidized crystalline molecular sieves are disclosed.

Metal oligomerization catalysts in general are more sensitive to feed impurities, (e.g., water, carbon monoxide, dienes, etc.) then are the acid catalysts. Although homogeneous, metal catalysts are quite active, the need for dry feeds, solvents, and other measures to prevent catalyst deactivation and precipitation is disadvantageous and suggests an obvious advantage to supported, heterogeneous, metal catalyst. Homogeneous acid catalysts are effective but are also corrosive and tend to form two liquid-phase systems with the non-polar hydrocarbon oligomerization products. Considering the foregoing observations, heterogeneous acid catalysts are the preferred red catalyst for use in the oligomerization step of the present invention. Of the heterogeneous acid catalysts, acid zeolites are especially preferred, particularly zeolites of the ZSM-type and borosilicates.

The oligomerization step of the present invention may be generally performed according to any of the numerous processes known to those skilled in the art.

The solid which is contacted with methane in the methane conversion step of one specific embodiment of the present process has heretofore been generally referred to as an oxidative synthesizing agent. Oxidative synthesizing agents comprise at least one oxide of at least one metal, which oxides when contacted with methane at temperatures selected within the range of about 500° to 1000° C. produce higher hydrocarbon products, coproduct water and a reduced metal oxide. The composition thus contains at least one reducible oxide of at least one metal. The term "reducible" identifies those oxides of metals which are reduced by the methane contact. The term "oxide(s) of metal(s)" includes: (1) one or more metal oxides (i.e., compounds described by the general formula $M_xO_y$ wherein M is a metal and the subscripts x and y designate the relative atomic proportions of metal and oxide in the composition) and/or (2) one or more oxygencontaining metal compounds, provided that such oxides and compounds have the capability of performing to produce higher hydrocarbon products as set forth herein.

Effective agents for the conversion of methane to higher hydrocarbons have previously been found to comprise reducible oxides of metals selected from the group consisting of manganese, tin, indium, germanium, antimony, lead, bismuth and mixtures thereof. Alkali and alkaline earth metals and compounds have been found to improve the hydrocarbon product selectivity of these agents. The further incorporation of phosphorus into agents promoted by alkali or alkaline earth components enhances catalyst stability.

Reducible oxides of cerium, praseodymium, and terbium have also been found to be effective for the conversion of methane to higher hydrocarbons when the rare earth component is associated with an alkali metal component (i.e., lithium, sodium, potassium, rubidium, cesium and compounds thereof).

The metal components may be associated with other support materials such as silica, magnesia, alumina, titania, zirconia and the like and combinations thereof. When employing agents containing rare earth components—oxides of Ce, Pr and Tb—the rare earth oxides preferably serve as supports.

Reducible oxides of manganese have been found to be particularly desirable for methane conversion, especially when associated with an alkali metal (preferably sodium). Especially preferred agents comprise silica- and/or magnesia-supported agents containing oxides of manganese and sodium.

Operating temperatures for the methane step conversion invention are generally within the range of about 500° to 1000° C. If reducible oxides of metals such as In, Ge or Bi are present in the solid, the particular temperature selected may depend, in part, on the particular reducible metal oxide(s) employed. Thus, reducible oxides of certain metals may require operating temperatures below the upper part of the recited range to minimize sublimation or volatilization of the metals (or compounds thereof) during methane contact. Examples are: (1) reducible oxides of indium, (operating temperatures will preferably not exceed about 850° C.); (2) reducible oxides of germanium (operating temperatures will preferably not exceed about 850° C.); and (3) reducible oxides of bismuth (operating temperatures will preferably not exceed about 850° C.).

Operating pressures for the methane contacting step are not critical to the presently claimed invention. However, both general system pressure and partial pressure of methane have been found to effect overall results. Preferred operating pressures are within the range of about 1 to 30 atmospheres.

Contacting methane and a reducible metal oxide to form higher hydrocarbons from methane also produces a reduced metal oxide and co-product water. The exact nature of the reduced metal oxides are unknown, and so are referred to herein as "reduced metal oxides". Regeneration of a reducible metal oxide is readily accomplished by contacting such reduced materials with oxygen (e.g., an oxygen-containing gas such as air) at elevated temperatures, preferably at a temperature selected within the range of about 300° to 1200° C., the particular temperature selected depending on the metal(s) included in the solid.

In carrying out the first step of the present process, a single reactor apparatus containing a fixed bed of solids may be used with intermittent or pulsed flow of a first gas comprising methane and a second gas comprising oxygen (e.g., oxygen, oxygen diluted with an inert gas, or air, preferably air). The methane contacting step and the oxygen contacting step may also be performed in physically separate zones with solids recirculating between the two zones.

Thus, a suitable method for synthesizing hydrocarbons from a methane source comprises: (a) contacting a gas comprising methane and particles comprising at least one reducible oxide of at least one metal to form higher hydrocarbon products, co-product water, and reduced metal oxide; (b) removing particles comprising reduced metal oxide from the first zone and contacting the reduced particles in a second zone with an oxygen-containing gas to form particles comprising a reducible metal oxide; and (c) returning the particles produced in the second zone to the first zone. The steps are preferably repeated at least periodically, and more preferably the steps are continuous. In the more preferred embodiment solids are continuously circulated between at least one methane-contact zone and at least one oxygen-contact zone.

The effluent produced by the methane conversion step of the method of this invention comprises unconverted methane and higher hydrocarbons, as well as carbon oxides and water. It is within the scope of the present invention to remove carbon oxides and water from the methane conversion effluent prior to further treatment of the effluent in accordance with the present invention.

Whether or not such intermediate separations are employed, a gas stream comprising normally gaseous olefins containing a major amount of $C_1$–$C_5$ alkanes is oligomerized to produce higher hydrocarbon products, preferably normally liquid hydrocarbon product.

What is claimed is:

1. A process for converting methane to higher hydrocarbon products which comprises:
   (a) contacting at a temperature selected within the range of about 500° to 1000° C. a gas comprising methane and at least one reducible oxide of at least one metal which oxides when contacted with methane at said temperature are reduced and produce higher hydrocarbon products and water, said contacting producing an effluent comprising normally gaseous olefins containing a major amount of unreacted methane and other higher, normally gaseous, alkanes; and (b) oligomerizing said effluent to produce higher hydrocarbon products.

* * * * *